United States Patent [19]

Riedel

[11] Patent Number: 6,069,011
[45] Date of Patent: May 30, 2000

[54] METHOD FOR DETERMINING THE APPLICATION OF A SAMPLE FLUID ON AN ANALYTE STRIP USING FIRST AND SECOND DERIVATIVES

[75] Inventor: Richard A. Riedel, Carmel, Ind.

[73] Assignee: UMM Electronics, Inc., Indianapolis, Ind.

[21] Appl. No.: 08/988,304

[22] Filed: Dec. 10, 1997

[51] Int. Cl.⁷ .................................................. G01N 33/49
[52] U.S. Cl. ............................ 436/34; 436/95; 436/164; 422/82.01; 422/82.02; 422/82.05
[58] Field of Search .................................. 436/34, 63, 95, 436/164, 166, 169; 422/56, 58, 68.1, 82.05, 82.02, 82.01; 435/4, 14, 25, 28, 805, 808

[56] References Cited

U.S. PATENT DOCUMENTS

| | | | |
|---|---|---|---|
| 3,298,789 | 1/1967 | Mast | 435/14 |
| 3,307,392 | 3/1967 | Owen et al. | 73/64.43 |
| 3,458,287 | 7/1969 | Gross et al. | 436/69 |
| 3,630,957 | 12/1971 | Rey et al. | 436/66 |
| 3,658,480 | 4/1972 | Kane et al. | 436/69 |
| 3,881,992 | 5/1975 | Ralston | 435/3 |
| 4,420,566 | 12/1983 | Jessop et al. | 436/46 |
| 4,935,346 | 6/1990 | Phillips et al. | 435/14 |
| 5,049,487 | 9/1991 | Phillips et al. | 435/4 |
| 5,059,394 | 10/1991 | Phillips et al. | 422/68.1 |
| 5,246,858 | 9/1993 | Arbuckle et al. | 436/8 |
| 5,272,060 | 12/1993 | Hamamoto et al. | 435/14 |
| 5,304,467 | 4/1994 | Sakamoto et al. | 435/14 |
| 5,389,097 | 2/1995 | Bennett et al. | 606/34 |

FOREIGN PATENT DOCUMENTS

| | | |
|---|---|---|
| WO 90/14414 | 11/1990 | WIPO . |
| WO 95/05590 | 2/1995 | WIPO . |

*Primary Examiner*—Maureen M. Wallenhorst
*Attorney, Agent, or Firm*—Woodard, Emhardt, Naughton, Moriarty & McNett Patent and Trademark Attorneys

[57] ABSTRACT

A method for determining the application of a sample fluid on an analyte strip using first and second derivatives. Sample fluid, such as whole blood, is applied to a reagent matrix and sensor readings, such as reflectance readings or current readings, are taken of the fluid/reagent combination. The first and second derivatives of the sensor readings are calculated. A predetermined incubation time period is begun at either a local minimum in the first derivative or a local maximum following a local minimum in the second derivative data. At the expiration of the incubation period, another sensor reading is taken which is indicative of an analyte concentration in the sample fluid (such as glucose concentration in a whole blood sample).

16 Claims, 8 Drawing Sheets

METHOD FOR DETERMINING THE APPLICATION OF A SAMPLE FLUID ON AN ANALYTE STRIP USING FIRST AND SECOND DERIVATIVES

TECHNICAL FIELD OF THE INVENTION

The present invention generally relates to a method for determining the application of chemical and biochemical components (analytes) in aqueous fluids on an analyte test strip and, more particularly, a method for determining the application of a sample fluid on an analyte strip using first and second derivatives.

BACKGROUND OF THE INVENTION

The quantification of chemical and biochemical components in colored aqueous fluids, in particular colored biological fluids such as whole blood and urine and biological fluid derivatives such as serum and plasma, is of ever-increasing importance. Important applications exist in medical diagnosis and treatment and in the quantification of exposure to therapeutic drugs, intoxicants, hazardous chemicals and the like. In some instances, the amounts of materials being determined are either so miniscule—in the range of a microgram or less per deciliter—or so difficult to precisely determine that the apparatus employed is complicated and useful only to skilled laboratory personnel. In this case, the results are generally not available for some hours or days after sampling. In other instances, there is often an emphasis on the ability of lay operators to perform the test routinely, quickly and reproducibly outside a laboratory setting with rapid or immediate information display.

One common medical test is the measurement of blood glucose levels by diabetics. Current teaching counsels diabetic patients to measure their blood glucose level from two to seven times a day depending on the nature and severity of their individual cases. Based on the observed pattern in the measured glucose levels the patient and physician together make adjustments in diet, exercise and insulin intake to better manage the disease. Clearly, this information should be available to the patient immediately.

Previously, a method widely used in the United States employs a test article of the type described in U.S. Pat. No. 3,298,789 issued Jan. 17, 1967 to Mast. In this method a sample of fresh, whole blood (typically 20–40 $\mu l$) is placed on an ethylcellulose-coated reagent pad containing an enzyme system having glucose oxidase and peroxidase activity. The enzyme system reacts with glucose and releases hydrogen peroxide. The pad also contains an indicator which reacts with the hydrogen peroxide in the presence of peroxidase to give a color proportional in intensity to the sample's glucose level.

Another previous blood glucose test method employs similar chemistry but in place of the ethylcellulose-coated pad employs a water-resistant film through which the enzymes and indicator are dispersed. This type of system is disclosed in U.S. Pat. No. 3,630,957 issued Dec. 28, 1971 to Rey et al.

In both cases the sample is allowed to remain in contact with the reagent pad for a specified time (typically one minute). Then in the first case the blood sample is washed off with a stream of water while in the second case it is wiped off the film. The reagent pad or film is then blotted dry and evaluated. The evaluation is made either by comparing color generated with a color chart or by placing the pad or film in a diffuse reflectance instrument to read a color intensity value.

While the above methods have been used in glucose monitoring for years, they do have certain limitations. The sample size required is rather large for a finger stick test and is difficult to achieve for some people whose capillary blood does not express readily.

In addition, these methods share a limitation with other simple lay-operator colorimetric determinations in that their result is based on an absolute color reading which is in turn related to the absolute extent of reaction between the sample and the test reagents. The fact that the sample must be washed or wiped off the reagent pad after the timed reaction interval requires that the user be ready at the end of the timed interval and wipe or apply a wash stream at the required time. The fact that the reaction is stopped by removing the sample leads to some uncertainty in the result, especially in the hands of the home user. Overwashing can give low results and underwashing can give high results.

Another problem that often exists in simple lay-operator colorimetric determinations is the necessity for initiating a timing sequence when blood is applied to a reagent pad. A user will typically have conducted a finger stick to a obtain a blood sample and will than be required to simultaneously apply the blood from the finger to a reagent pad while initiating a timing circuit with his or her other hand, thereby requiring the use of both hand simultaneously. This is particularly difficult since it is often necessary to insure that the timing circuit is started only when blood is applied to the reagent pad. In order to eliminate the need for the user to initiate a timing sequence upon application of the blood sample to the reagent pad, U.S. Pat. No. 5,049,487 issued Sep. 17, 1991 to Phillips et al. teaches the use of a reagent pad and reflectance measurement system as illustrated schematically in FIG. 1. The Phillips et al. patent teaches an apparatus for determining the presence of an analyte in a fluid as well as a test strip for use with the apparatus. The fluid to be analyzed is applied to the test strip and the test strip is analyzed by the apparatus. In a preferred embodiment, the test strip comprises a single layer hydrophilic porous matrix 10 to which the chemical reagents are bound. The chemical reagents react with the analyte in the sample applied to the test strip in order to produce a dye that is characteristically absorptive at a wavelength other than the wavelength that the assay medium substantially absorbs. In other works, reaction of the chemical reagent with the analyte produces a color change in the sample.

The reagent matrix 10 is coupled to the underside of an inert test strip carrier 12 containing an orifice 14 therethrough. The analyte sample is applied to the orifice 14 and the apparatus analyzes the opposite side of the test strip by reflecting light from an LED 16 off of the bottom surface of the reagent matrix 10 and sensing the amount of reflected light with a photodiode 18. It is therefore necessary for the sample to diffuse through the test strip prior to being analyzed. In such systems, the amount of time that the analyte is allowed to react with the reagent prior to measurement of a color change is critical to the accuracy of the measurement. The beginning of this "incubation period" must be measured as precisely as possible. In the Phillips et al. patent, as the analyte sample penetrates the reagent matrix 10 and wets the bottom surface, an initial change in reflectance of this measurement surface occurs. The apparatus detects this change in reflectance by sensing a decrease in the amount of light reflected to the photodetector 18. The apparatus then begins the incubation period upon detection of this change in reflectance. After a predetermined incubation time period, during which the sample containing the analyte reacts with the reagent chemicals in the matrix 10, a second reflectance measurement is made in order to determine the color change in the sample. By accurately measuring the beginning of the incubation period and the time delay before measurement, the accuracy of the apparatus is greatly improved over prior methods.

As shown in FIG. 2, the Phillips et al. method could also be adapted to an electrochemical measurement system, in which changes in conductivity of the reagent pad 10 are measured by a current meter 20. Two electrodes 22, 24 are placed in contact with the reagent pad 10 and a voltage source 26 is coupled across the electrodes 22, 24. The amount of current measured by the current meter 20 is directly proportional to the conductivity of the reagent pad 10, which conductivity changes as the blood glucose reacts with the reagent.

Because the start of the incubation period in the Phillips et al. method begins with a determination that surface wetting of the underside of the reagent matrix 10 has occurred (in the embodiment of FIG. 1), the processing circuitry coupled to the photodetector 18 must have some method for determining when the reflectance measurements indicate surface wetting. Referring to FIG. 3, there is shown a graph of remission (percent reflection) v. the apparatus system time (in which one unit of system time equals 0.25 seconds of actual time). As can be seen from the graph, the reflectivity of the reagent matrix 10 prior to sample application is a constant value (approximately 88%). After sample application, the reflectivity of the underside of the reagent matrix 10 steadily drops as the sample fluid migrates to the underside of the reagent matrix 10. The remission also drops due to a color change in the reagent caused by reaction with the analyte sample. At some point, the analyte fluid has reached the undersurface of the reagent matrix 10 and further drops in remission are caused only by color change of the reagent. The prior art method analyzes this data in order to make a determination of when surface wetting has occurred on the underside of the reagent matrix 10. This determination is made by sensing when the remission value has dropped by a predetermined, fixed amount from its steady state value prior to sample application. For example, in one commercial version of this prior art system, surface wetting is assumed to have occurred when the remission value drops by approximately 38% (i.e. when a remission value of 50% is observed). When this change in remission (or $\Delta R$) is observed, the prior art device starts the timing of the incubation period, after which the sample measurement will be made.

As shown in FIG. 4, the prior art Phillips et al. method can be adapted to the electrochemical sensor apparatus of FIG. 2, since the measured current exhibits a sharp increase upon application of the sample. The start of the incubation period may therefore be started when the current increases by more than a predetermined, fixed amount.

The prior art method described in Phillips et al. suffers from the problem that the start of the incubation period, by using a fixed reflectance drop, must be tailored to a specific chemistry. A changing in the base reflectance, such as may occur for different enzymes or indicators, requires a predetermination of the fixed reflectance drop. In this sense, a given fixed drop is not generally applicable to different systems.

SUMMARY OF THE INVENTION

The present invention relates to a method for determining the application of a sample fluid on an analyte strip using first and second derivatives. Sample fluid, such as whole blood, is applied to a reagent matrix and sensor readings, such as reflectance readings or current readings, are taken of the fluid/reagent combination. The first and second derivatives of the sensor readings are calculated. A predetermined incubation time period is begun at either a local minimum in the first derivative or a local maximum following a local minimum in the second derivative data. At the expiration of the incubation period, another sensor reading is taken which is indicative of an analyte concentration in the sample fluid (such as glucose concentration in a whole blood sample).

The present invention provides a method which is more generally applicable to different systems. By keying the start of reaction timing to the physics of the system via the first and second derivatives, one creates an algorithm, which is independent of the magnitude of the variable in question. This is true whether the variable is electrical current such as measured in an electrochemical system, or reflectance such as is measured in a colorimetric system. In addition to providing a method that is more generally applicable than the prior art Phillips et al. method, by using the maximum or minimum values of the first or second derivatives, one eliminates the need for experimentation to determine what is the "best" fixed drop. In sharp contrast to the prior art, there are no human input factors in the present invention, the start of timing being fixed entirely by the dynamics of hydration and color development, which are determined by the physics of the strip.

In one form of the invention, a method for determining a start of reaction timing for measurement of a reaction between a sample fluid and a reagent is disclosed comprising the steps of: a) measuring the reagent at intervals prior to application of the sample fluid to the reagent; b) applying the sample fluid to the reagent; c) measuring the reagent/sample fluid combination at intervals after performing step (b); d) calculating a first derivative of the measurement data taken at steps (a) and (c); e) determining a location of a local minimum in the first derivative data; f) beginning a predetermined time period at a time corresponding to the local minimum; and g) measuring the reagent/sample fluid combination after expiration of the predetermined time period.

In another form of the invention, a method for determining a start of reaction timing for measurement of a reaction between a sample fluid and a reagent is disclosed comprising the steps of: a) measuring the reagent at intervals prior to application of the sample fluid to the reagent; b) applying the sample fluid to the reagent; c) measuring the reagent/sample fluid combination at intervals after performing step (b); d) calculating a second derivative of the measurement data taken at steps (a) and (c); e) determining a location of a local maximum following a local minimum in the second derivative data; f) beginning a predetermined time period at a time corresponding to the local maximum; and g) measuring the reagent/sample fluid combination after expiration of the predetermined time period.

DETAILED DESCRIPTION OF THE PREFERRED EMBODIMENTS

Figure 1:
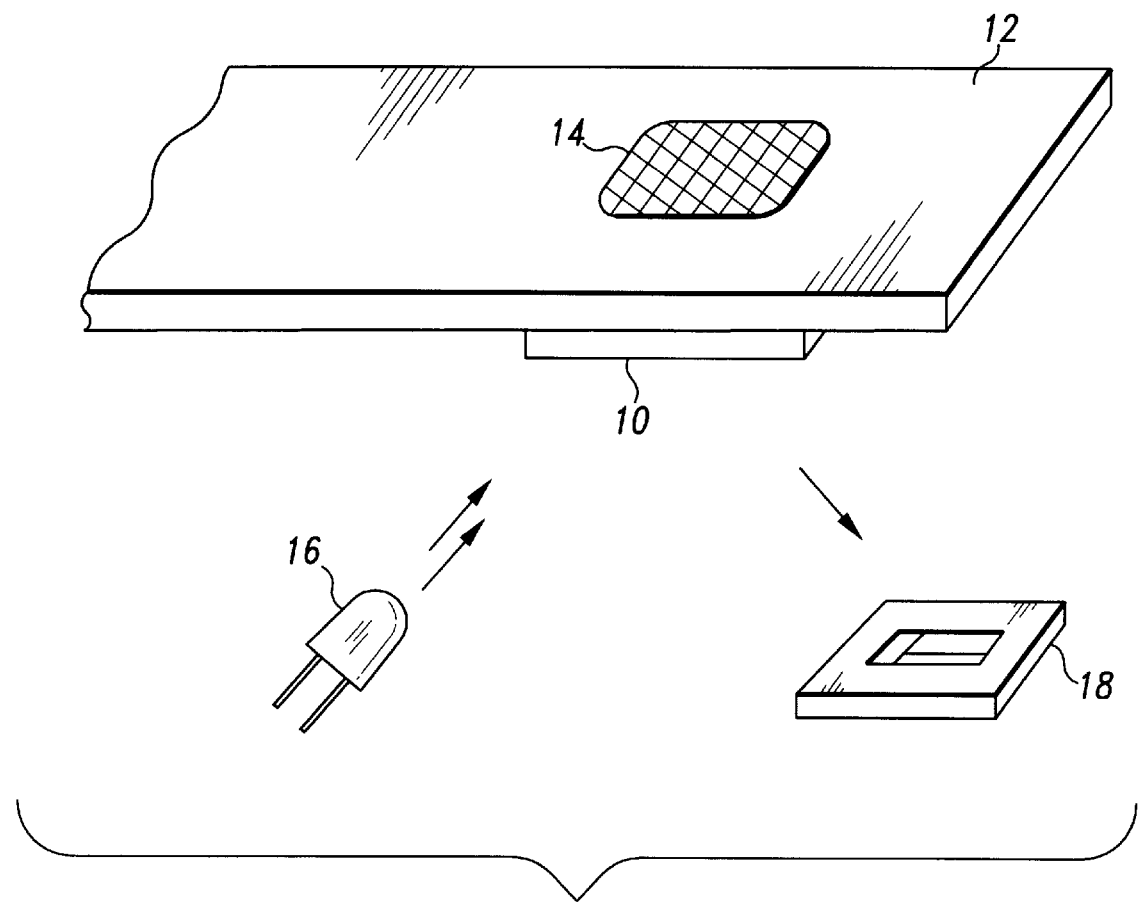
FIG. 1 is a schematic perspective view of a prior art optical reflectance analyte measurement system.
Figure 2:
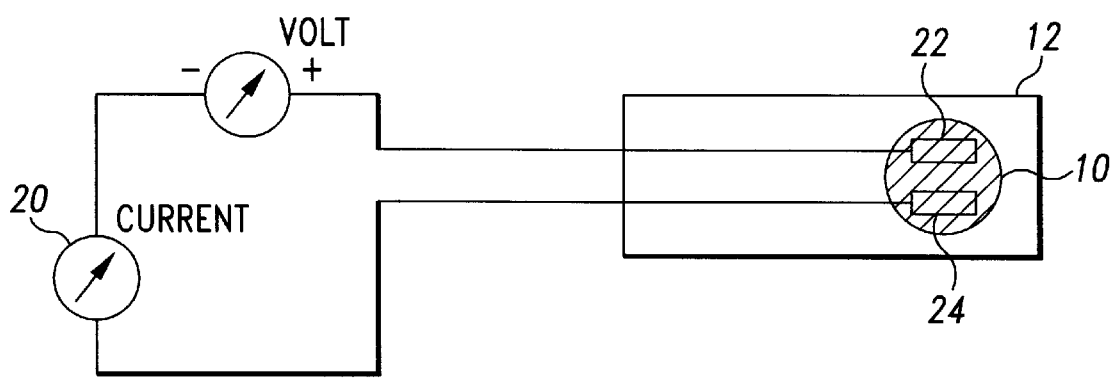
FIG. 2 is a schematic diagram of a prior art electrochemical analyte measurement system.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 3:
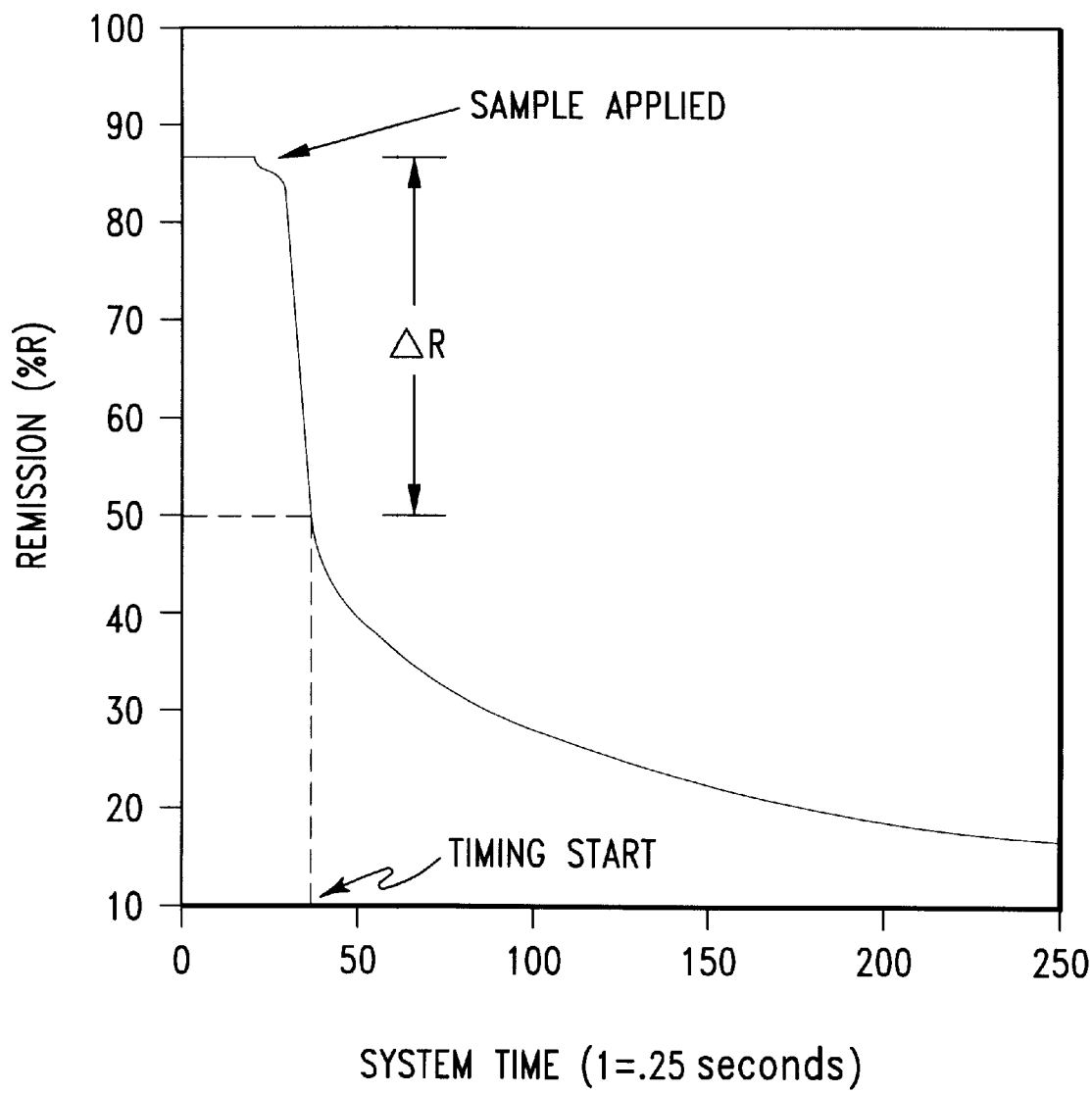
FIG. 3 is a graph of remission v. system time, illustrating a prior art method for determining a start of the reaction incubation period in an optical reflectance meter.
Figure 5:
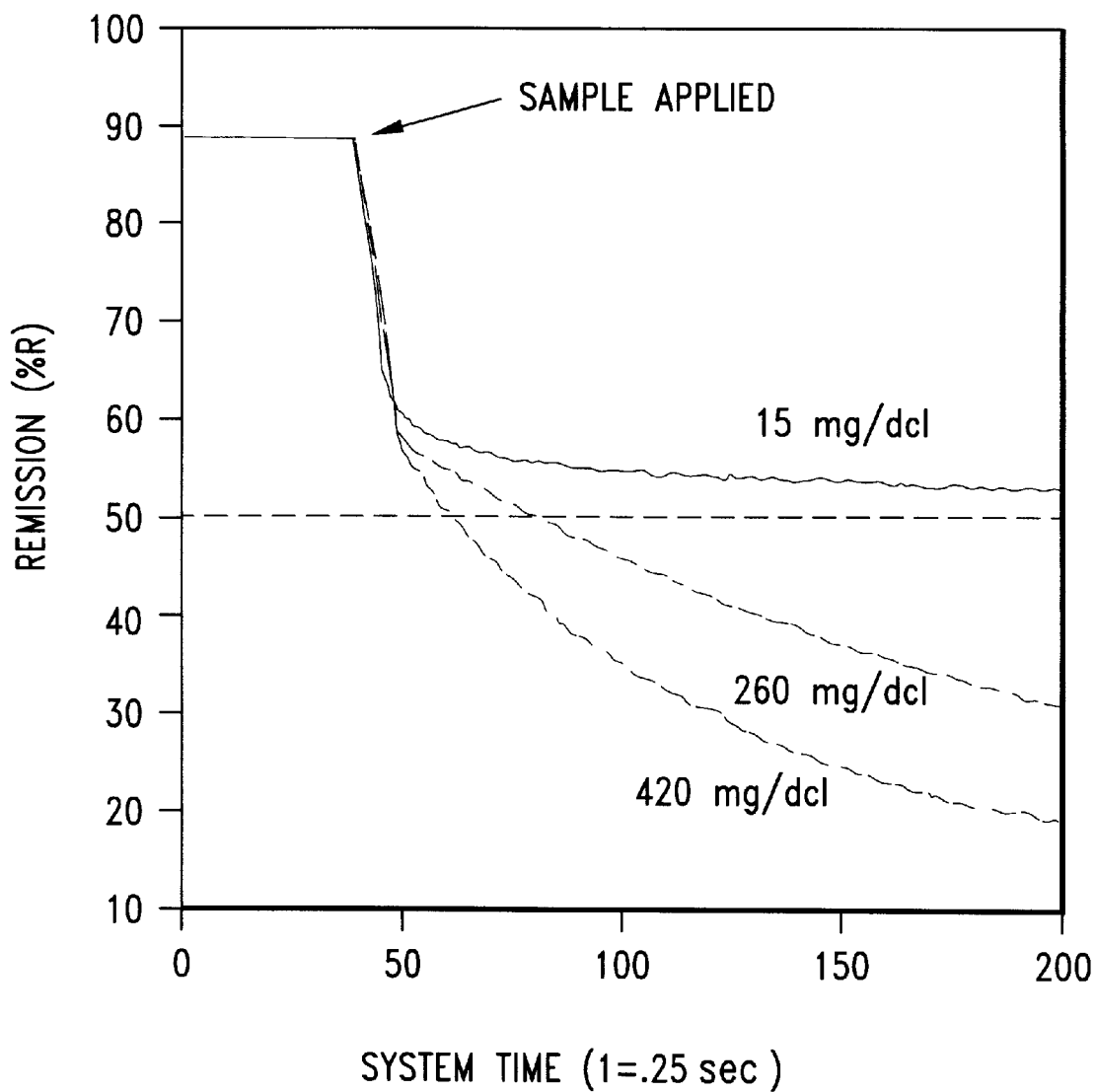
FIG. 5 is a graph of remission v. system time for several different analyte samples.

FIG. 5 illustrates the problem with establishing the start of the incubation period with a predetermined drop in remission. It is characteristic of remission v. time data for a whole blood sample to exhibit the general shape of the curve of FIG. 3. However, FIG. 5 plots the remission v. time data for several different whole blood samples, illustrating that the minimum remission value and the speed with which the graph transitions to the minimum remission value is highly variable and dependent upon several factors, including the glucose concentration within the sample. Therefore, while picking a predetermined drop in remission value in order to start the incubation period may work well when the remission v. time graph has the expected form (as in FIG. 3), this method may not work well when the remission v. time graph for different glucose samples varies widely, as shown in FIG. 5. The 50% remission threshold of FIG. 3 is not effective for the varying curves of FIG. 5, as plainly evident from an examination of this figure. In fact, one of the remission v. time curves never reaches the 50% remission value. Utilizing a predetermined drop in remission at the start of the incubation period is therefore undesirable in many real-world test scenarios. For the chemistry of FIG. 5 it is obvious that reducing the magnitude of the predetermined drop will cause a start time for all three curves. However, it is by no means certain that the same magnitude will be valid for a chemistry where the background material has a different density, or the enzyme-indicator mix has a different base color. In theory, it is possible that n different strip lots could require n different "predetermined" drops.

Figure 6:
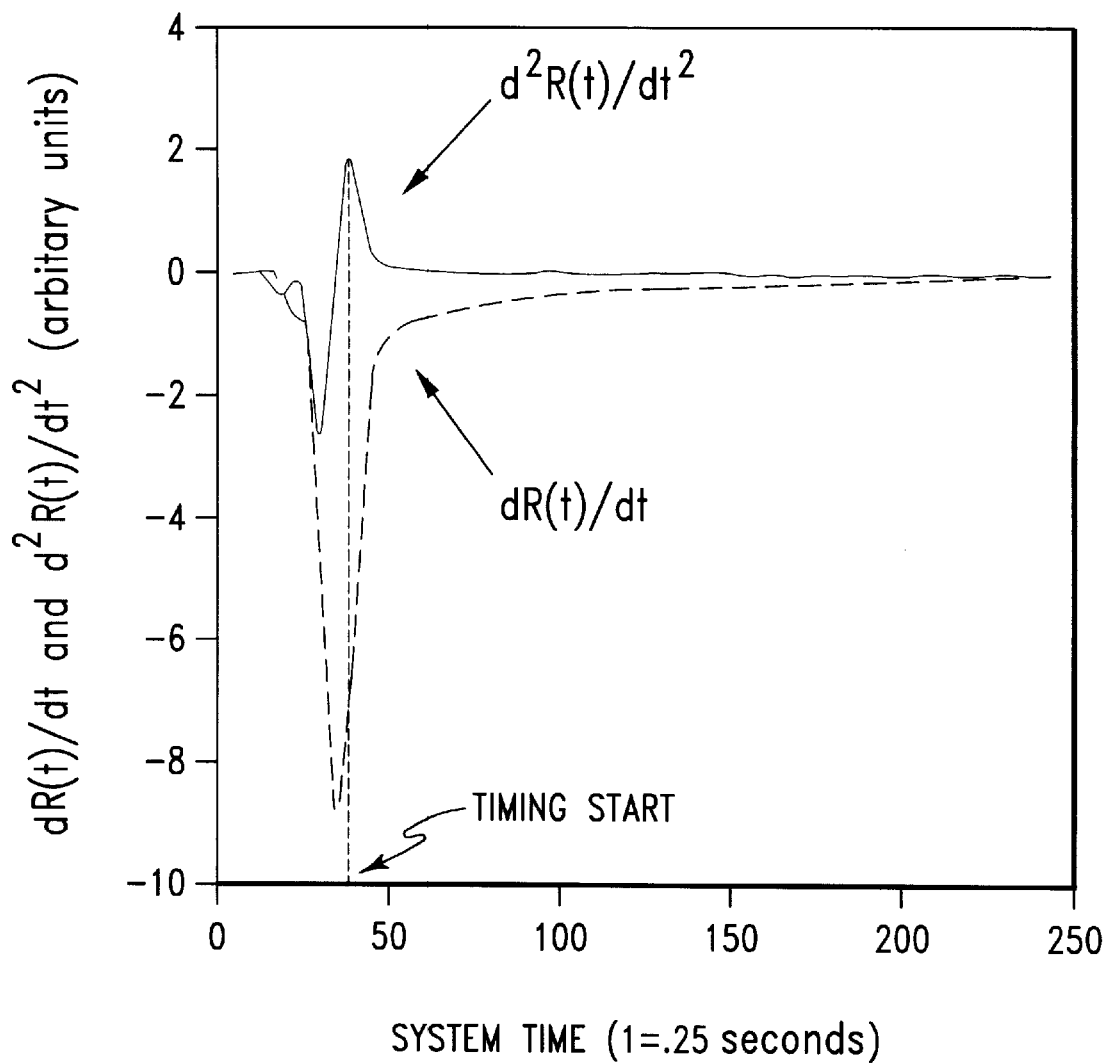
FIG. 6 is a graph of the first derivative and second derivative of the remission data of FIG. 3.

The present invention relies upon an analysis of the first and/or second derivatives of the remission v. time data in order to determine the start of the incubation period. FIG. 6 illustrates both the first derivative and the second derivative of the remission v. time data of FIG. 3. The first derivative data (dR(t)/dt) is a measure of the speed at which the remission value is changing v. time. The second derivative data ($d^2R(t)/dt^2$) is a measure of the acceleration or deceleration of the first derivative speed. The shape of the graphs in FIG. 6 is characteristic for remission data taken from whole blood samples. No matter how steep or how shallow the remission v. time curve, the first derivative data will always exhibit a well-defined minimum before leveling off to a value which is substantially zero. Additionally, the second derivative data will always exhibit a well-defined minimum followed by a well-defined maximum before leveling off to a value which is substantially zero. The present invention utilizes this consistent behavior in the second derivative data in order to identify the start of reaction timing (i.e. the start of the incubation period). The start of reaction timing is established at the peak of the local maximum in the second derivative data (which closely coincides with the maximum in the second derivative data), as illustrated in FIG. 6. Alternatively, acceptable results can often be obtained by starting the reaction timing at the minimum in the first derivative data, thereby obviating the need for the apparatus to calculate the second derivative data and reducing processor overhead.

The second derivative method of the present invention represents an improvement over the prior art method that measures wetting of the undersurface of the reagent matrix. Because the second derivative method analyzes the dynamic change of the remission values, color development within the reagent matrix plays an important role in locating the maximum in the second derivative. When using the second derivative method of the present invention, one can clearly see changes in the established start time of the incubation period as a function of glucose concentration. When only sensing wetting of the undersurface of the reagent matrix, as in the prior art method, the glucose concentration of the analyte sample has no effect on the establishment of the start of reaction timing. This is why the prior art method does not perform well in the situation illustrated in FIG. 5. However, the second derivative method of the present invention performs well in establishing the start of reaction timing for whole blood samples having a broad range of glucose concentrations because the present method relies upon color development within the testing reagent to effect the dynamics of the rate of change of the remission values, and hence the establishment of the start of reaction timing.

Figure 4:
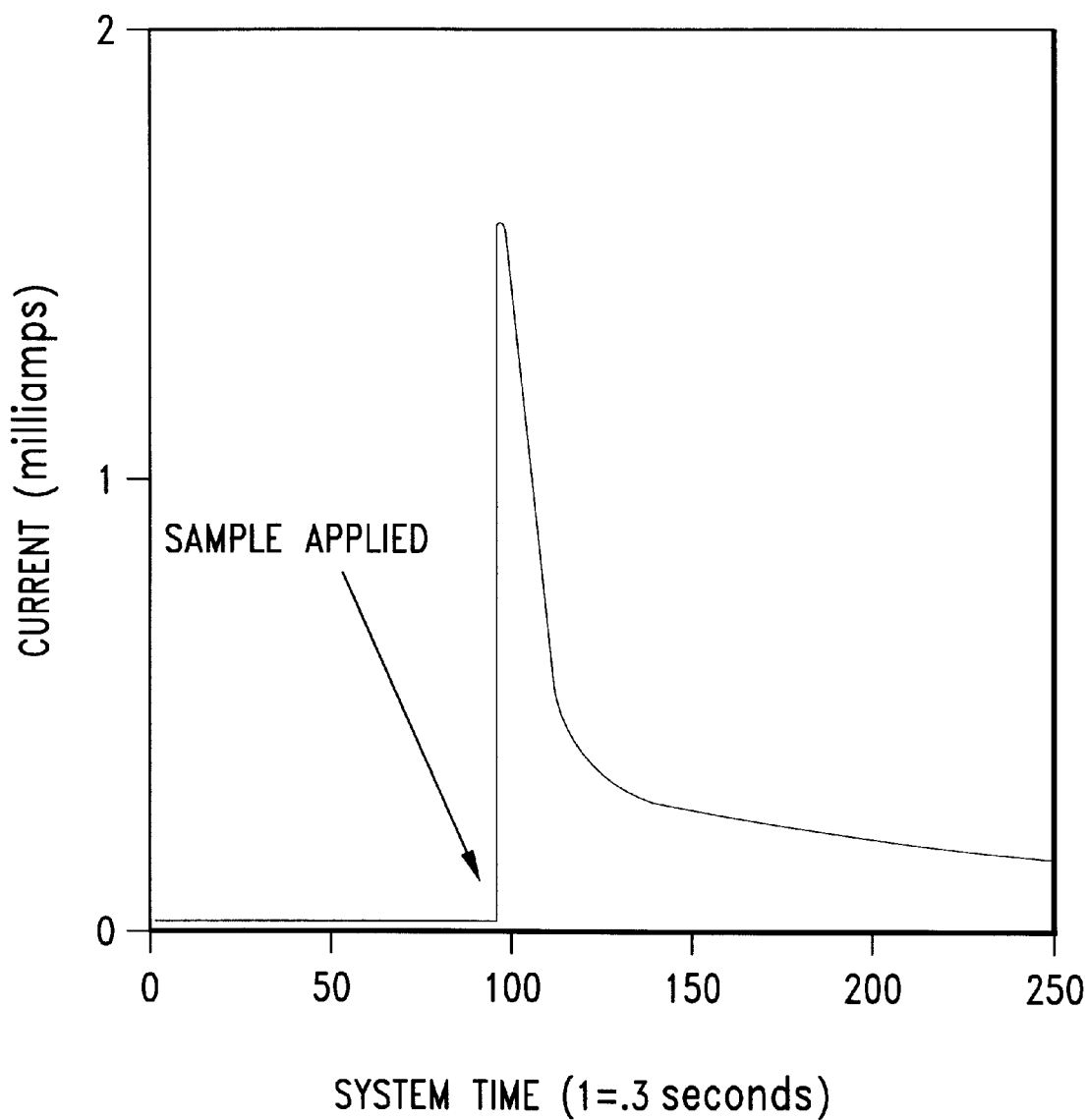
FIG. 4 is a graph of current v. system time, illustrating a prior art method for determining a start of the reaction incubation period in an electrochemical meter.
Figure 7:
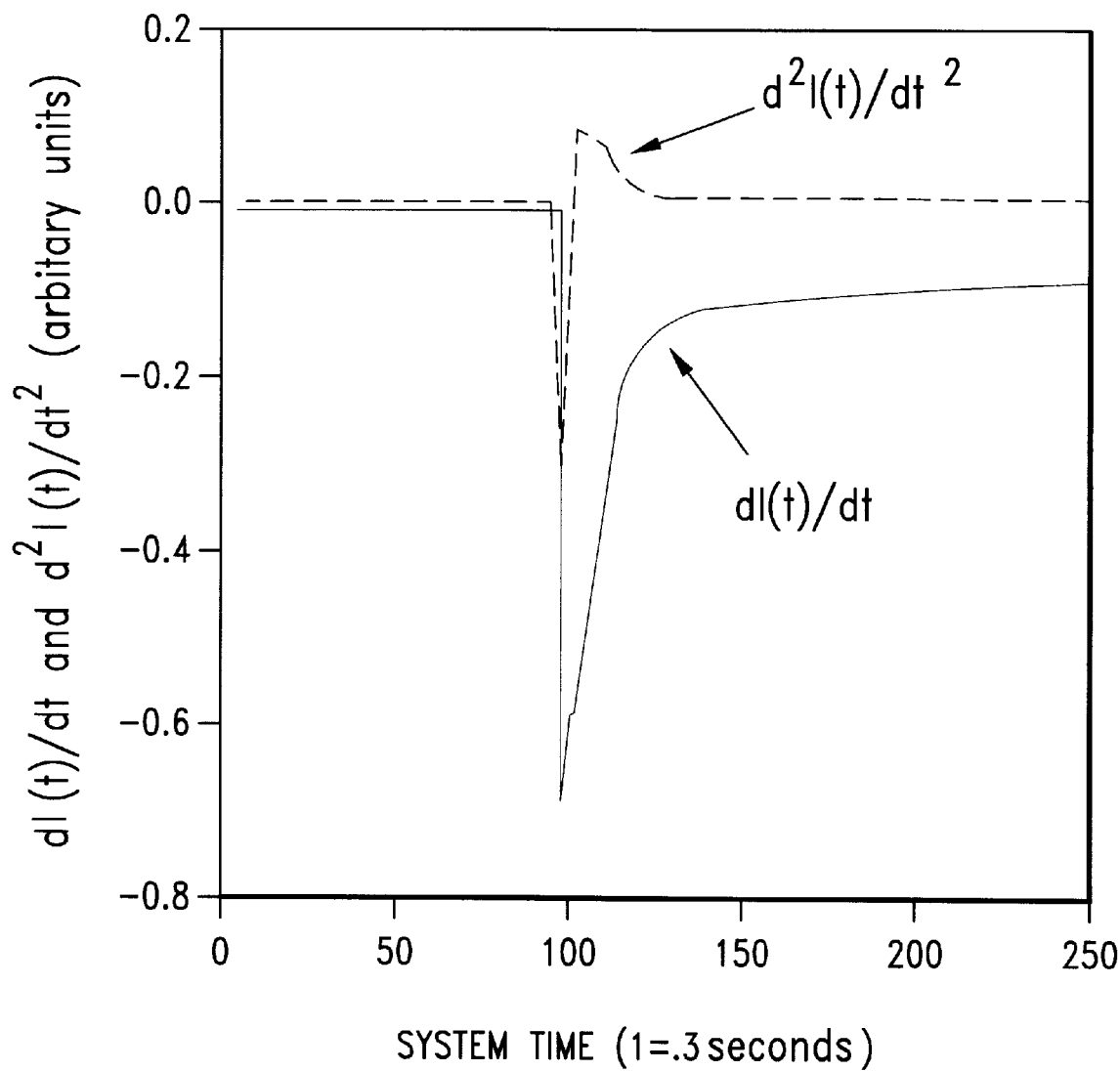
FIG. 7 is a graph of the first derivative and second derivative of the current data of FIG. 4.

Referring to FIG. 7, there is illustrated both the first derivative and the second derivative of the electrochemical sensor data of FIG. 4. As can be seen, the data of FIG. 7 exhibits the same shape characteristics as the data of FIG. 6, therefore the first and second derivative methods for determining the start of the incubation period described hereinabove can be applied equally well to the electrochemical sensor data.

It will be appreciated by those skilled in the art that, rather than initiating the incubation period based upon a predetermined drop in remission (when using a reflectance measurement apparatus), the method of the present invention measures the speed of change in the reflectance readings and begins the incubation period when the speed of change in the reflectance readings begins to slow down. It is this feature that allows this method of the present invention to accurately predict the start of reaction timing for samples having a wide variance in glucose concentrations. Because the start of reaction timing in the present invention is initiated upon the occurrence of a local maximum in the second derivative data, the difference in the remission data from the initial reading to the reading at the start of reaction timing will therefore not be a constant value as with the prior art predetermined-drop method. Instead, use of the second derivative method of the present invention will produce different values of remission at the start of reaction timing depending upon the actual shape of the remission v. time curve. In other words, although the start of reaction timing for any remission v. time curve will occur at the local maximum point at the second derivative, these starting points do not correspond to any consistent amount of drop in remission value from the initial reading to the reading at the start of reaction timing. This is plainly demonstrated in the results of the following test.

Data from 19 separate runs was used for this test. Test conditions for the different test runs were varied in order to simulate expected variations in glucose concentration, hematocrit levels, dosage volume and temperature. The composition of the samples applied to the test strips is summarized in Table I.

TABLE 1

Test Sample Composition

| No. of Data Points | Glucose Spike (mg/dcl) | Hematocrit (%) | Dose Volume (ml) | Blood Temp. (° C.) |
|---|---|---|---|---|
| 4 | 45 | 40 | 20 | R.T. |
| 1 | 45 | 40 | 20 | 15 |
| 1 | 45 | 40 | 20 | 35 |
| 5 | 160 | 40 | 20 | R.T. |
| 1 | 160 | 40 | 20 | 15 |
| 1 | 160 | 40 | 20 | 35 |
| 1 | 290 | 40 | 20 | R.T. |
| 1 | 160 | 50 | 20 | R.T. |
| 1 | 160 | Control | 20 | R.T. |
| 1 | 160 | 30 | 20 | R.T. |
| 1 | 290 | 30 | 4 | R.T. |
| 1 | 45 | 40 | 4 | R.T. |

The control solution was a mixture of BSA and electrolytes, spiked with glucose. The blood samples (and the control sample) were applied to the test strips using a pipette.

The raw test data for each sample was obtained using a reflectance test meter coupled to a computer that requests an A/D count from the meter every 0.33 seconds. An initial reading was taken with no test strip in the meter. A second reading was then taken after the test strip was inserted into the meter, but before it was dosed. Upon dosing, readings were taken every 0.33 seconds. Remission values were computed using a defined blank strip remission of 88%.

The second derivative timing start mechanism of the present invention was applied to the test data by establishing the start time when the second derivative of the remission data transitioned through a local minimum followed by a local maximum. The start time was established at this local maximum point for each of the test runs.

Figure 8:
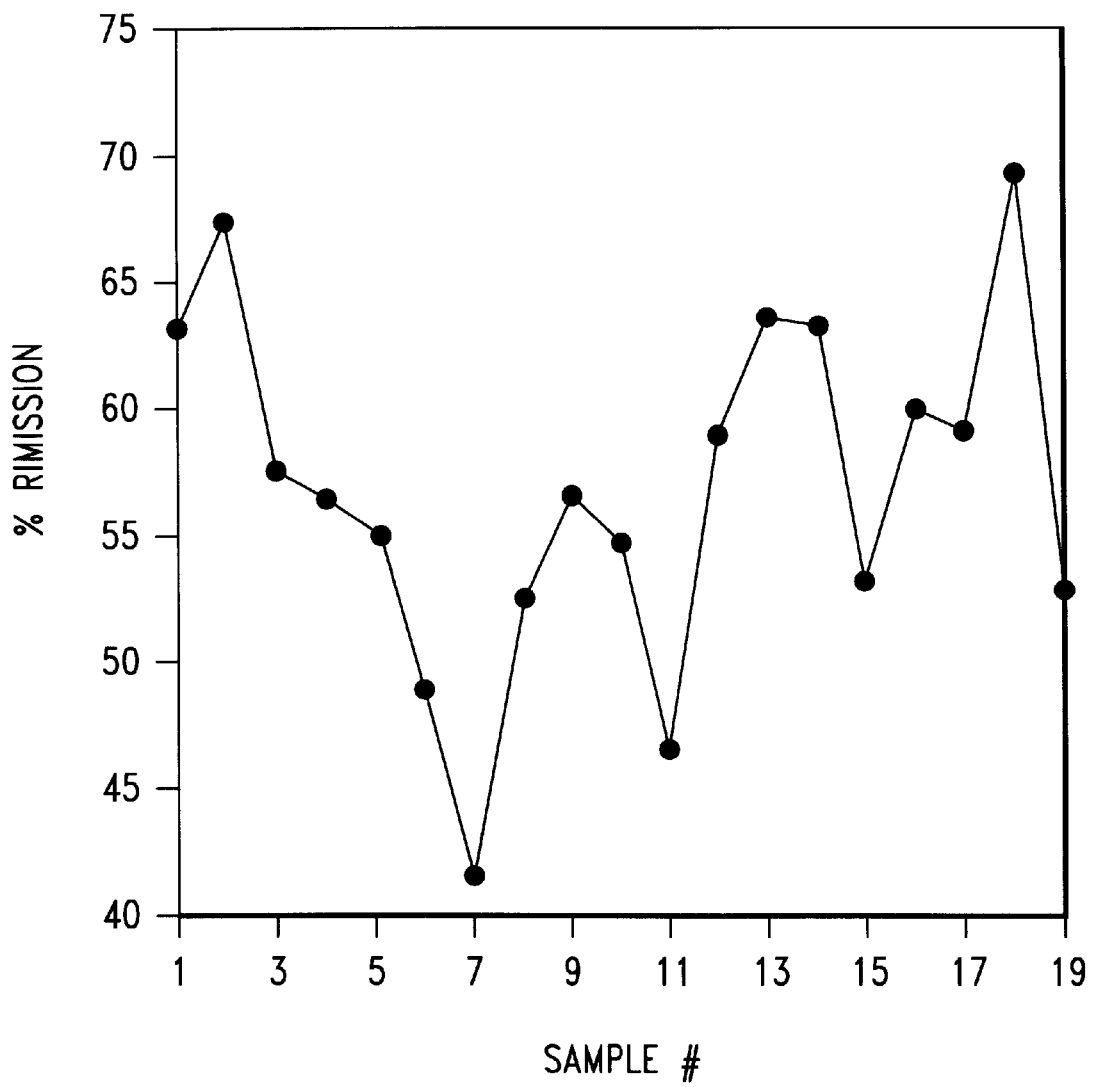
FIG. 8 is a graph of the start times established by the second derivative timing start mechanism for 19 test runs vs. the percentage remission value.

Because incubation period start time of the present invention is not based upon the actual remission value, but instead upon the rate of change of the change in the remission values, the remission value at the start of timing is unpredictable. As illustrated in FIG. 8, the start times established by the second derivative timing start mechanism for each of the 19 test runs occurred at a remission value ranging between 42% and 69% (a variation of 27% remission). This wide variation in remission values underscores the fact that the second derivative method more accurately determines the start of reaction between the analyte fluid and the reagent than is possible by sensing surface wetting in the prior art predetermined drop method.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for determining a start of reaction timing for measurement of a reaction between a sample fluid and a reagent, comprising the steps of:

a) measuring light reflected from the reagent at intervals prior to application of the sample fluid to the reagent;

b) applying the sample fluid to the reagent, thereby creating a reagent/sample fluid combination;

c) measuring light reflected from the reagent/sample fluid combination at intervals after performing step (b);

d) calculating a first derivative of measurement data taken at steps (a) and (c);

e) determining a location of a local minimum in the first derivative;

f) beginning a predetermined time period at a time corresponding to the local minimum, wherein the predetermined time period corresponds to a time for reaction between the sample fluid and reagent; and g) measuring light reflected from the reagent/sample fluid combination after expiration of the predetermined time period.

2. The method of claim 1, wherein the sample fluid is whole blood.

3. The method of claim 2, wherein the reagent reacts with the whole blood to produce a color change in proportion to an amount of glucose in the whole blood.

4. The method of claim 1, wherein the intervals are fixed intervals.

5. A method for determining a start of reaction timing for measurement of a reaction between a sample fluid and a reagent, comprising the steps of:

a) measuring light reflected from the reagent at intervals prior to application of the sample fluid to the reagent;

b) applying the sample fluid to the reagent, thereby creating a reagent/sample fluid combination;

c) measuring light reflected from the reagent/sample fluid combination at intervals after performing step (b);

d) calculating a second derivative of measurement data taken at steps (a) and (c);

e) determining a location of a local maximum following a local minimum in the second derivative;

f) beginning a predetermined time period at a time corresponding to the local maximum, wherein the predetermined time period corresponds to a time for reaction between the sample fluid and reagent; and g) measuring light reflected from the reagent/sample fluid combination after expiration of the predetermined time period.

6. The method of claim 5, wherein the sample fluid is whole blood.

7. The method of claim 6, wherein the reagent reacts with the whole blood to produce a color change in proportion to an amount of glucose in the whole blood.

8. The method of claim 5, wherein the intervals are fixed intervals.

9. A method for determining a start of reaction timing for measurement of a reaction between a sample fluid and a reagent, comprising the steps of:

a) measuring current flowing through the reagent at intervals prior to application of the sample fluid to the reagent;

b) applying the sample fluid to the reagent, thereby creating a reagent/sample fluid combination;

c) measuring current flowing through the reagent/sample fluid combination at intervals after performing step (b);

d) calculating a first derivative of measurement data taken at steps (a) and (c);

e) determining a location of a local minimum in the first derivative;

f) beginning a predetermined time period at a time corresponding to the local minimum, wherein the predetermined time period corresponds to a time for reaction between the sample fluid and reagent; and g) measuring current flowing through the reagent/sample fluid combination after expiration of the predetermined time period.

10. The method of claim 9, wherein the sample fluid is whole blood.

11. The method of claim 10, wherein the reagent reacts with the whole blood to produce a color change in proportion to an amount of glucose in the whole blood.

12. The method of claim 9, wherein the intervals are fixed intervals.

13. A method for determining a start of reaction timing for measurement of a reaction between a sample fluid and a reagent, comprising the steps of:

a) measuring current flowing through the reagent at intervals prior to application of the sample fluid to the reagent;

b) applying the sample fluid to the reagent, thereby creating a reagent/sample fluid combination;

c) measuring current flowing through the reagent/sample fluid combination at intervals after performing step (b);

d) calculating a second derivative of measurement data taken at steps (a) and (c);

e) determining a location of a local maximum following a local minimum in the second derivative;

f) beginning a predetermined time period at a time corresponding to the local maximum, wherein the predetermined time period corresponds to a time for reaction between the sample fluid and reagent; and g) measuring current flowing through the reagent/sample fluid combination after expiration of the predetermined time period.

14. The method of claim 13, wherein the sample fluid is whole blood.

15. The method of claim 14, wherein the reagent reacts with the whole blood to produce a color change proportion to an amount of glucose in the whole blood.

16. The method of claim 13, wherein the intervals are fixed intervals.

* * * * *